(12) United States Patent
Chesne

(10) Patent No.: US 8,415,139 B2
(45) Date of Patent: Apr. 9, 2013

(54) METHOD FOR PACKAGING CELLS IN CULTURE IN A LOW-PRESSURE ENVIRONMENT, AND CORRESPONDING DEVICE

(75) Inventor: Christophe Chesne, Vannes (FR)

(73) Assignee: SARL Biopredic International, Rennes (FR)

( * ) Notice: Subject to any disclaimer, the term of this patent is extended or adjusted under 35 U.S.C. 154(b) by 0 days.

(21) Appl. No.: 12/440,735

(22) PCT Filed: Sep. 6, 2007

(86) PCT No.: PCT/EP2007/059355
§ 371 (c)(1),
(2), (4) Date: Oct. 7, 2009

(87) PCT Pub. No.: WO2008/031759
PCT Pub. Date: Mar. 20, 2008

(65) Prior Publication Data
US 2010/0062528 A1 Mar. 11, 2010

(30) Foreign Application Priority Data

Sep. 13, 2006 (FR) ..................................... 06 08019

(51) Int. Cl.
*C12M 1/00* (2006.01)
*C12M 3/00* (2006.01)
*C12N 1/00* (2006.01)
*C12N 5/00* (2006.01)
*C12N 5/02* (2006.01)

(52) U.S. Cl. .................. 435/283.1; 435/243; 435/307.1; 435/325

(58) Field of Classification Search .................. None
See application file for complete search history.

(56) References Cited

U.S. PATENT DOCUMENTS

| 5,842,573 A | 12/1998 | Halvorsen |
| 2005/0235368 A1 | 10/2005 | Xiao |

FOREIGN PATENT DOCUMENTS

| EP | 1085081 | 3/2001 |
| FR | 2682980 | 4/1993 |
| FR | 2689139 | 10/1993 |
| JP | 11151083 A | 8/1999 |
| JP | 2005304501 A | 4/2005 |

*Primary Examiner* — Debbie K Ware
(74) *Attorney, Agent, or Firm* — Thomas Horstemeyer, LLP

(57) ABSTRACT

Method for packaging cells in culture in a low-pressure environment, and corresponding device. The invention relates to a method for packaging live cells in culture for the purpose of transporting them, wherein said cells are in a culture medium contained in at least one container, characterized in that said method comprises: a phase of filling said container(s) according to a given degree of filling; a step of closure of said container(s) comprising: bagging said container(s) in a flexible sachet; and reducing the pressure inside said sachet; sealing said sachet, with the pressure reduction being maintained, wherein said closure step is carried out under temperature conditions correlated with said degree of filling with a view to avoiding the boiling of said culture medium during said pressure reduction.

13 Claims, 1 Drawing Sheet

METHOD FOR PACKAGING CELLS IN CULTURE IN A LOW-PRESSURE ENVIRONMENT, AND CORRESPONDING DEVICE

CROSS REFERENCE TO RELATED APPLICATION

This application claims priority to "Method for Packaging Cells in Culture in a Low-Pressure Environment, and Corresponding Device," having serial number PCT/EP2007/059355, filed on Sept. 6, 2007. This application also claims priority to and benefit of French Application entitled "Method for Packaging Cells in Culture in a Low-Pressure Environment, and Corresponding Device", having Application No. 0608019, filed on Sept. 13, 2006, which is incorporated by reference in its entirety.

The field of the invention is that of the packaging of cells in culture with a view to the transport thereof. More specifically, the invention relates to a method for packaging cells in culture medium contained in containers, or in wells comprised in plates.

The marketing of cells in the form of ready-to-use culture plates requires a transport phase between the producer and/or the distributor and the end user. The culture plates cannot be transported as is because no system is envisaged to prevent the culture medium from coming out of the wells, due to spillage. However, cells cannot survive during transport without being in direct continuous contact with the culture medium.

Various technical solutions are used for this transport step.

The most frequently used and least expensive technical solution consists of covering the plates filled with culture medium with an adhesive plastic film. The use of adhesive films to seal culture plates is confronted with various types of problems, such as the release of potentially toxic products.

Moreover, a residual volume forming an air bubble is most frequently present in the wells (100% filling of the wells being very difficult to obtain). Said air bubbles trapped under the film must be expelled manually using a syringe, for each well: air bubbles may in fact come into contact with the cells during transport, particularly in the event of the reversal of single-layer cell plates, and are liable to cause the damage or death of the cells. In this case, it is necessary to cover the plate with a second adhesive plastic film to seal the holes made by the syringe. Therefore, this plate preparation process for transport involves the drawback of being long and therefore non-productive in industrial terms.

In addition, the external temperature during transport is liable to vary considerably, particularly in the case of distant transport by air. This causes dilations and retractions of the packaging materials, resulting in the loss of tightness thereof, which causes the leakage of the culture medium outside the wells of the multi-well plates, as they are not sealed. Moreover, the use of adhesive films for the transport of plates having large wells (6-well plates in particular) does not make it possible to ensure the tightness thereof, as the weight of the liquid in the wells is greater than the adhesion force of the adhesive film.

Heat-sealable films also exist, wherein the adhesion force is greater than adhesives, but the seal is difficult to reverse and leaves marks when the seal is removed, which is not acceptable for the end customer.

Other multi-well sealing systems are used, such as plastic or rubber caps to be placed on the wells. The drawbacks of this system are also numerous. Firstly, the cost price of said sealing system is high, which renders it difficult to use in this industrial sector. However, the main limitation of said cap sealing systems is the poor tightness thereof due to dimensional variations of the wells in the same plate or between plate batches. In order to resolve this problem, it is possible to use flexible caps, but in this case the presence of caps on the wells reduces the volume of transport medium in each well by ⅔. Said medium volume available above the cells is insufficient to ensure the supply of nutrient and to ensure pH stability throughout transport, which may last for 3 days.

Another drawback is that it is necessary to have one cap model per plate type, while a single solution, that can be fitted on all types of substrates, would be more advantageous in industrial terms.

A technique is also known from the patent application FR 2862980 filed on behalf of the applicant, consisting of rendering the transport medium solid, by adding polysaccharide polymer powder. The addition of said polymer grains to the culture medium results in the formation of a compact hydrogel on the cells, thus getting around the problem of leakages due to a solidification of the transport medium. In practice, it was found that this system required significant development to ensure the neutrality of the hydrogel on each different cell type. Moreover, the appearance of the polymers was difficult for the end user to accept.

Another transport system, described in the US patent application 2005/0235368 was developed for the transport of a specific type of cells: transgenic *Xenopus laevis* ovocytes. According to this transport method, the sealing is carried out by pressing a silicone plate on the wells. This pressure is applied by means of compression.

None of said technical solutions definitively resolve the problems of the long-distance transport phase, either that of the leakages observed more or less frequently, or that of the volume of the transport medium (cap solution).

The aim of the invention is to remedy the drawbacks of the prior art.

More specifically, the aim of the invention is to propose a technique for packaging cells in culture intended to be transported, which is more reliable than the techniques of the prior art, particularly in terms of preservation of cell quality.

The aim of the invention is also to provide such a technique which makes it possible to fill containers with culture medium with a high degree of filling.

The aim of the invention is also to provide such a technique, making it possible to ensure the tightness of containers.

The aim of the invention is also to provide such a technique with any or practically any type of plate.

A further aim of the invention is to provide such a technique which is easy and inexpensive to use.

These aims, along with others which will emerge hereinafter, are achieved by means of the invention which relates to a method for packaging cells in culture for the purpose of transporting them, wherein said cells are in a culture medium contained in at least one container, characterised in that said method comprises:

a phase of filling said container(s) according to a given degree of filling;

a step of closure of said container(s) comprising:

bagging said container(s) in a flexible sachet;

reducing the pressure inside said sachet;

sealing said sachet, the pressure reduction being maintained, wherein said closure step is carried out under temperature conditions correlated with said degree of filling in order to avoid the boiling of said culture medium during said pressure reduction.

In this way, the invention proposes a technical solution making it possible to ensure the tightness, not by means of a compression method as in US patent 2005/0235368, but by means of a pressure reduction method, carried out by means of bagging the culture plates in a partial vacuum.

Such a technique can be used with any type of commonly used plate, said plates possibly having from 6 to 3456 wells.

It is noted that the technical solution proposed by the invention is intended to seal the wells, wherein the vacuum sealing method needs to be reversible.

This solution goes against the practices of the field of the invention, in that it is known that cell cultures cannot withstand a strong vacuum (i.e. a final pressure of almost 0 bar), said conditions resulting in boiling of the cell transport medium, which impairs the viability of the cells. For this reason, no person skilled in the art had previously envisaged said method intended to ensure tightness by means of pressure reduction.

In fact, during the reduction of the pressure in the culture wells, "bubbling" of the transport medium above the cells is observed. Said bubbling is due to a rapid degassing of the transport medium. The gases dissolved in said media at atmospheric pressure partly return to the gaseous state during the reduction of the pressure (essentially $O_2$, $CO_2$, $N_2$).

Therefore, it is crucially important to prevent said degassing.

In addition to the fact that such bubbling induces splashes, it modifies the acid-base equilibrium of the medium and the cultured cells.

Said acid-base equilibrium is in fact produced by a carbonate-bicarbonate buffer, which makes it possible to solubilise $CO_2$ according to the following reaction: $CO_2+H_2O$ gives $HCO_3^-+H^+$.

Degassing, even partial, of the solution induces alkalinisation of the medium, which is toxic for the cells.

It is noted that boiling may be induced by other physico-chemical phenomena, induced by the combination of the pressure, volume and temperature parameters.

In any case, bubble formation is liable to cause the detachment of the cells from the well, which are then resuspended in the medium. In this case, at the time of opening by the operator, the removal of the medium to access the cells (supposed to be at the bottom of the wells) results in the loss of the cells. By adjusting the temperature and filling parameters according to various embodiments which will be explained hereinafter, the invention proposes a technical solution to prevent said bubble formation, which makes it possible to respect the acid-base equilibrium of the cells, work under cleanliness conditions in accordance with the cell culture and prevent moistening (caused by splashing due to boiling) of the edges of the wells (containers) from impeding the tight closure thereof.

The technical solution according to the invention is twofold: adjust the temperature and the volume of medium, or more precisely the volume of gas left above the medium in the wells.

Preferentially, said filling phase is preceded by a temperature rise step of said culture medium such that said culture medium displays a temperature corresponding to said temperature conditions.

According to an advantageous solution, said pressure reduction step is carried out so as to obtain a pressure in said container between approximately 20 millibars and approximately 120 millibars after said closure step, and more preferentially to obtain a pressure of approximately 60 millibars.

Indeed, it is observed that when the vacuum is too strong, below approximately 20 millibars, the cells start to show signs of distress and above 120 millibars, the vacuum is insufficient to ensure a homogenous pressure on the closure elements of the wells and may not ensure the absence of leaks.

According to a first approach of the invention, said containers are filled substantially completely with said culture medium and said pressure reduction step is conducted while said culture medium displays a temperature greater than 0° C. and less than approximately 20° C., and preferentially while said culture medium displays a temperature of approximately 4° C.

In this way, the reduction in the temperature of the medium delays the degassing time during the reduction of the external pressure.

It is noted that, below 0° C., the cells freeze, and above 20° C., the boiling phenomenon becomes excessive.

According to a second approach of the invention, said pressure reduction step is conducted while said culture medium displays a temperature greater than approximately 20° C. and less than approximately 37° C., said containers being filled with said culture medium with a degree of filling between approximately 70% and approximately 95%, and preferentially with a degree of filling of approximately 90%.

Below 70% filling, it is observed that a large air bubble remains in the wells following the packaging method, said air bubble being liable to damage the viability of the culture if prolonged contact with the cell sheet occurs during transport.

Above 95% filling, the medium overflows during the packaging method. Due to said adjustment of the filling volume, the degassing induced by the pressure drop to which the packaging system is subjected will be attenuated by the presence of a small quantity of air in the wells (approximately 10%).

This limits the bubbling of the medium and thus preserves the integrity of the cell sheet.

According to a preferred embodiment of the invention, said closure step comprises a positioning step on said container of a closure material liable to be deformed.

Such a deformable material may therefore fit the wells and fit the contour thereof perfectly, which ensures perfect tightness of the closure.

In this case, said closure material advantageously displays a mean hardness of 60 Shores, said closure material being preferentially an elastomer material.

The deformability and flexibility of the elastomer material are important, as said plate should not be too rigid, because it would not fit the well correctly, or too flexible, which causes deformation during the application of a vacuum in the system, said deformation being liable to create leaks.

According to a preferred solution, the method comprises a covering step of said closure material with a rigid securing material.

The closure material being made of flexible material, it may tend, in some cases, to be deformed in the wells, at the risk of displaying heterogeneities around the wells, which favours leaks.

The purpose of the rigid plastic plate positioned above the elastomer plate is to provide a given rigidity to the closure system, and enable the pressure created by the reduction in atmospheric pressure to be distributed homogeneously on the entire culture plate.

This plate also makes it possible to obtain improved cell preservation, due to the gas tightness thereof.

The invention also relates to packaging of live cells in culture intended to be transported by means of the method described above, said packaging including at least one container at least partially filled with a culture medium containing said cells, and a sachet containing said container(s), and being characterised in that said container(s) is/are maintained in a vacuum in said sachet.

Preferentially, said container(s) is/are closed by a closure material liable to be deformed.

Also preferentially, the packaging comprises a rigid securing material plate covering said closure material of the container.

Other features and advantages of the invention will emerge more clearly on reading the following description of two preferential embodiments thereof, given as illustrative and non-limitative examples, and the appended figures wherein.

As specified above, the principle of the invention lies in the fact that creating a pressure reduction around the packaging system for transport which, by indirectly applying a constant high pressure in a homogeneously distributed manner on the closure means, ensures the transport of the plates without medium leakage.

Figure 1:
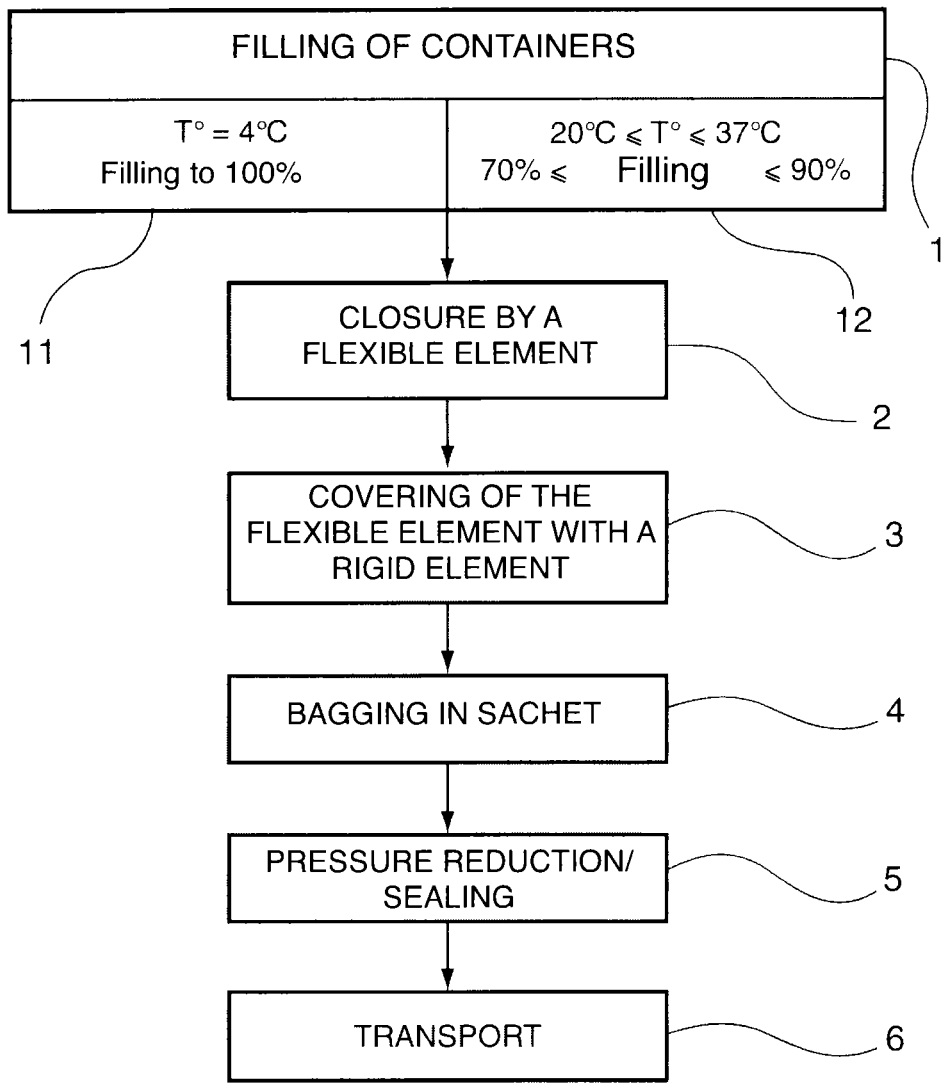
FIG. 1 is a synoptic representation of a method according to the invention.

With reference to FIG. 1, the first step 1 consists of filling the containers with a given degree of filling explained below.

The closure of the wells comprises a step 2 consisting of mounting on the wells an elastomer material preferentially displaying a hardness of 60 Shores.

Said material is sterilised by means of usual sterilisation techniques before use.

During step 3, a rigid securing material, preferentially a rigid transparent material, is mounted on the elastomer plate.

The following step 4 comprises the bagging of the containers closed by the elastomer and rigid plates in sachets.

During step 5, suction of the air contained in the sachets is carried out. The sachet is sealed while the pressure reduction inside the sachet is carried out, by means of a technique known per se.

The pressure parameters are controlled precisely by the device responsible for applying the vacuum.

Various devices can be used to produce the vacuum with a satisfactory setting precision, in a 20-second cycle to produce a very precise vacuum and seal a sachet during step 5 mentioned above.

Therefore, the closure of each of the wells is carried out by pressing an elastomer plate on the edges of the wells. The tightness is ensured when the pressure reduction created by the vacuum exerts a sufficient force to attach the elastomer plate with the well edges, by means of the linings of the sachet.

During tests conducted, the formation of bubbling of the transport medium at 37° C. during the application of the vacuum at 60 millibars was rapidly detected. The boiling generating splashes on the well edges prevents the tight dry contact of the elastomer plate on the edges of the well. The medium contained in the well then moves by means of capillarity outside the well when the plate is shaken with a little vigour. The tightness of the system is not guaranteed.

It would appear that said boiling or the effects thereof can be limited for the same vacuum, by means of:
partial filling of the well; or
cooling of the culture media at 4° C.

In the case of partial filling (corresponding to step 12), the culture medium is preheated between 20° C. and 37° C. (preferentially 37° C.), the well being filled with a degree of filling comprised between 70% and 95%, preferentially 90%.

The drawback of the partial filling is that the ability of the packaging to preserve the cell sheet becomes limited in the event of reversal of the plate during transport. In fact, the air bubble present in the well is large and may in some cases dry the cell sheet in the event of prolonged contact.

In the case of a medium cooled at 4° C. (corresponding to step 11), the wells are filled with 3.25 ml of culture medium (=100% of the volume of liquid that can be introduced into a well, accounting for the presence of a meniscus).

During the application of the vacuum at 60 millibars, the medium cooled at 4° C. does not "bubble", therefore the boiling point is lowered.

Splashes and air contact problems in the case of prolonged reversal of the culture plate no longer occur.

The results of the tests are given in table 1 below.

TABLE 1

| Vacuum (millibars) | Culture medium temperature | Well filling level (%) | 'Boiling' | Tightness ensured |
|---|---|---|---|---|
| 60 | 37° C. | 100% (=3.25 ml) | yes | no |
| 60 | 37° C. | 75% (=2.40 ml) | yes | yes |
| 60 | 4° C. | 100% (=3.25 ml) | no | yes |

In the context of the present examples of embodiments, it was confirmed that tightness is ensured for a vacuum level greater than or equal to 60 millibars (60->0 millibars). However, a significant deformation of the elastomer closure element was observed above 40 millibars (40->0 millibars). For a lower vacuum level (less than 60 millibars and almost up to atmospheric pressure), leakages of culture medium were observed when the culture plate was shaken with some vigour.

Tests were carried out on primary hepatocyte cultures in 24-well plates.

These cells were selected for the development of said new transport system as they are among the most sensitive (fragile). By determining ideal conditions for said cells, said conditions are optimised for other more resistant cell types such as lines.

Primary hepatocyte cultures were packaged in a vacuum for 72 hours before being returned to culture under the usual conditions. The morphological observations are given in table 2 below.

TABLE 2

| Condition | Vacuum (millibars) | Culture medium temperature | Well filling level (%) | Elastomer plate quality | Addition of securing plate | Tightness ensured | Appearance of cells |
|---|---|---|---|---|---|---|---|
| 1 | 60 | 37° C. | 75% (=2.40 ml) | Elastomer thickness 4 mm, 86 × 128 mm | no | yes | Good hepatic morphology, Presence of dead cells |

TABLE 2-continued

| Condition | Vacuum (millibars) | Culture medium temperature | Well filling level (%) | Elastomer plate quality | Addition of securing plate | Tightness ensured | Appearance of cells |
|---|---|---|---|---|---|---|---|
| 2 | 60 | 37° C. | 75% (=2.40 ml) | Elastomer thickness 3 mm, 86 × 128 mm | no | yes | As above |
| 3 | 60 | 37° C. | 75% (=2.40 ml) | Elastomer for food, thickness 1 mm, 86 × 128 mm | no | yes | Very deformed elastomer plate, pressure reduction of silicone in each wells, weakened cells |
| 4 | 60 | 37° C. | 75% (=2.40 ml) | Elastomer thickness 4 mm, 86 × 128 mm | yes | yes | Very good hepatic morphology, less cells to detach (=dead cells) |
| 5 | 60 | 4° C. | 100% (=3.25 ml) | Elastomer thickness 4 mm, 86 × 128 mm | yes | yes | Very good hepatic morphology, less cells to detach (=dead cells) |

The addition of the rigid securing plate to limit the deformation of the elastomer plate and optimise the positioning thereof on the wells was also studied.

It is noted that, according to the results given in table 2, that the rigid securing plate improves results in terms of cell preservation, due to the gas tightness thereof (which is not the case of the elastomer plate alone).

Two types of sachets were tested to produce the outer packaging:
- a thick sachet;
- a flexible sachet.

During the vacuum packing (60 millibars), complete suction of the air is performed better in a flexible sachet.

Indeed, in a thick, rigid plastic sachet, the air remains trapped on the folds formed at each corner of the culture plate and suction is not complete. The closure of the containers by means of pressure reduction is therefore less reliable.

Primary hepatocyte cultures were vacuum packed by reproducing each of the best parameters determined above:
- vacuum produced at 60 millibars
- 100% filling of the well volume, with a transport medium cooled at 4° C.—3 mm thick elastomer plate
- addition of a rigid plate
- flexible sachet for outer packaging.

The correct preservation of the primary hepatocyte cultures was evaluated after 72 hours of packaging (maximum transport time required for cells currently in the laboratory), on morphological and enzymatic criteria. The results are represented in table 3 below.

TABLE 3

| | | Morphology | Nifedipine oxidase activity (CYP3A4/5) (nanomole/ hr/mg proteins): | Phenacetin O-deethylase activity (CYP1A2) (nanomole/ hr/mg proteins) | Paracetamol glucuronidation activity (nanomole/hr/mg proteins) | Paracetamol sulphation activity (nanomole/hr/mg proteins) |
|---|---|---|---|---|---|---|
| Primary culture No. 1 | Control in incubator 37° C., 95/5 air/CO2 | Refringent cells, nuclei and mb clearly visible, few dead cells | 2.1 | 0.5 | 3.7 | 1.6 |
| | Vacuum packed for 72 hrs, returned to culture in incubator 37° C., 95/5 air/CO2 | As for control | 1.8 | 0.6 | 4.5 | 2.0 |
| Primary culture No. 2 | Control in incubator 37° C., 5% CO2 | Refringent cells, nuclei and mb clearly visible | 3.0 | 0.2 | 5.8 | 3.9 |
| | Vacuum packed for 72 hrs, returned to culture in incubator 37° C., 95/5 air/CO2 | As for control | 1.6 | 0.2 | 6.8 | 3.9 |

During the transport step 5, the culture plates packaged in this way are shipped according to professional practices. According to said practices, the external temperature must be controlled. In addition, the system will be placed in a polyurethane isothermal box. These practices are not the subject matter of the invention.

Figure 2:
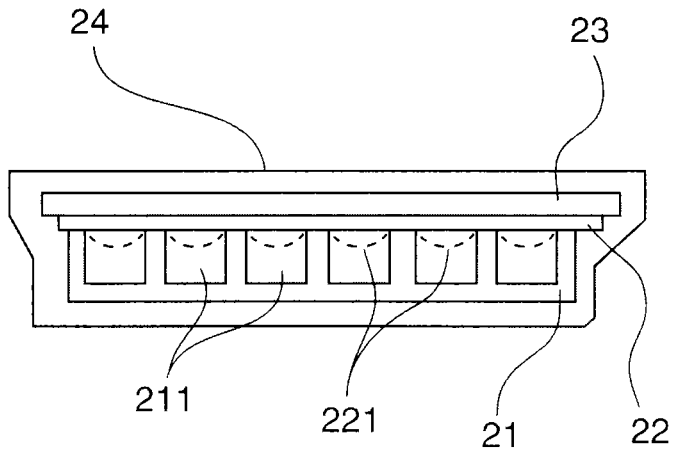
FIG. 2 is a schematic representation of a packaging produced by means of the method according to the invention.

On receipt, the end users must break the vacuum to retrieve the culture plates. This is performed without any special precaution other than the precautions ensuring the maintenance of sterility. The vacuum-packed sachet is cut, for example, simply using a pair of scissors. A packaging obtained by means of a method according to the invention is illustrated by FIG. 2.

Such a packaging consists of:
- a plate 21 displaying a plurality of wells 211 containing cells in culture medium in a partial vacuum;
- an elastomer plate 22 wherein the flexibility enables it to be deformed towards the inside of the wells (represented by the deformations 221 marked with dotted lines);
- a securing plate 23 (or transparent rigid plastic plate) securing the elastomer plate 22 on the wells;
- a sealed flexible sachet 24.

The invention claimed is:

1. A method for packaging live cells in culture for the purpose of transporting them, wherein said cells are in a culture medium contained in at least one container,
said method comprises:
a phase of filling said container(s) according to a given degree of filling;
a step of closure of said container(s) comprising:
bagging said container(s) in a flexible sachet;
reducing the pressure inside said sachet;
sealing said sachet, the pressure reduction being maintained,
wherein said closure step is carried out under temperature conditions correlated with said degree of filling in order to avoid the boiling of said culture medium during said pressure reduction and comprises a positioning step on said container of a closure material liable to be deformed.

2. A method for packaging live cells according to claim 1, wherein said filling phase is preceded by a temperature rise step of said culture medium such that said culture medium displays a temperature corresponding to said temperature conditions.

3. A method for packaging cells in culture according to claim 1, wherein said pressure reduction step is carried out so as to obtain a pressure in said container between approximately 20 millibars and approximately 120 millibars after said closure step.

4. A method for packaging cells in culture according to claim 3, wherein said pressure reduction step is carried out so as to obtain a pressure in said container of approximately 60 millibars after said closure step.

5. A method for packaging cells in culture according to claim 1, wherein said pressure reduction step is conducted while said culture medium displays a temperature greater than 0° C. and less than approximately 20° C., said containers being substantially completely filled with said culture medium.

6. A method for packaging cells in culture according to claim 5, wherein said pressure reduction step is conducted while said culture medium displays a temperature of approximately 4° C.

7. A method for packaging cells in culture according to claim 1, wherein said pressure reduction step is conducted while said culture medium displays a temperature greater than approximately 20° C. and less than approximately 37° C., said containers being filled with said culture medium with a degree of filling between approximately 70% and approximately 95%.

8. A method for packaging cells in culture according to claim 7, wherein said pressure reduction step is conducted while said culture medium displays a temperature greater than approximately 20° C. and less than approximately 37° C., said containers being filled with said culture medium with a degree of filling of approximately 90%.

9. A method for packaging cells in culture according to claim 1, wherein said closure material displays a mean hardness of approximately 60 Shores.

10. A method for packaging cells in culture according to claim 1, wherein said closure material is an elastomer material.

11. A method for packaging cells in culture according to claim 1, wherein it comprises a covering step of said closure material with a rigid securing material.

12. Packaging of live cells in culture intended to be transported obtained by means of the method according to claim 1, said packaging including at least one container (21) at least partially filled with a culture medium containing said cells, and a sachet (24) containing said container(s), wherein said container(s) (21) is/are maintained in a vacuum in said sachet (24) and is/are closed by a closure material (22) liable to be deformed.

13. Packaging according to claim 12, wherein it comprises a rigid securing material plate (8) covering said closure material of the container.

* * * * *

UNITED STATES PATENT AND TRADEMARK OFFICE
CERTIFICATE OF CORRECTION

PATENT NO.         : 8,415,139 B2  
APPLICATION NO.    : 12/440735  
DATED              : April 9, 2013  
INVENTOR(S)        : Christophe Chesne Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

First Day of September, 2015

Michelle K. Lee
*Director of the United States Patent and Trademark Office*